(12) United States Patent
Moore et al.

(10) Patent No.: US 10,816,526 B2
(45) Date of Patent: Oct. 27, 2020

(54) DEVICE AND METHOD FOR TESTING GAS DETECTOR

(71) Applicants: Ferrel D. Moore, Lincoln Park, MI (US); James Robert Moore, Dearborn, MI (US)

(72) Inventors: Ferrel D. Moore, Lincoln Park, MI (US); James Robert Moore, Dearborn, MI (US)

( * ) Notice: Subject to any disclaimer, the term of this patent is extended or adjusted under 35 U.S.C. 154(b) by 179 days.

(21) Appl. No.: 15/887,739

(22) Filed: Feb. 2, 2018

(65) Prior Publication Data
US 2018/0217116 A1    Aug. 2, 2018

Related U.S. Application Data

(60) Provisional application No. 62/453,700, filed on Feb. 2, 2017.

(51) Int. Cl.
*G01N 33/00* (2006.01)
(52) U.S. Cl.
CPC ....... *G01N 33/007* (2013.01); *G01N 33/0016* (2013.01); *G01N 2033/0072* (2013.01)
(58) Field of Classification Search
CPC .................. G01N 33/007; G01N 2033/0072
See application file for complete search history.

(56) References Cited

U.S. PATENT DOCUMENTS

| 6,632,674 B1 * | 10/2003 | Warburton | ......... G01N 33/0006 436/181 |
| 6,650,681 B1 * | 11/2003 | Ullman | ................. H01S 3/2215 372/34 |
| 7,640,783 B2 | 1/2010 | Eickhoff | |
| 2001/0018844 A1 | 9/2001 | Parekh | |
| 2006/0101925 A1 | 5/2006 | Peng et al. | |
| 2006/0150711 A1 | 7/2006 | Hong et al. | |
| 2008/0106170 A1 | 5/2008 | Knowles et al. | |
| 2013/0305807 A1 | 11/2013 | Wang et al. | |

FOREIGN PATENT DOCUMENTS

DE        102014108109      * 12/2015    ............. G01N 37/00

OTHER PUBLICATIONS

International Search Report and Written Opinion of related application PCT/US2018/016701 dated May 15, 2018, 12 pages.

* cited by examiner

*Primary Examiner* — Eric S. McCall
*Assistant Examiner* — Timothy P Graves
(74) *Attorney, Agent, or Firm* — Stinson LLP (57) ABSTRACT

A gas detector is tested by releasing detectable gas from a storage medium and delivering it to the gas detector. A cartridge for delivering detectable gas includes a container with an outlet and a storage medium in the container. Detectable gas is stored in the storage medium for being desorbed from the storage medium. A test device can include a receptacle for receiving the cartridge, an interface for fluidly coupling the device to a gas detector, and passaging to provide fluid communication between the interface and both the cartridge received in the receptacle and external air. A pump can pump external air and the detectable gas released from the cartridge through the passaging and interface such that the pumped detectable gas and air form a proportioned mixture for testing the gas detector.

20 Claims, 9 Drawing Sheets

DEVICE AND METHOD FOR TESTING GAS DETECTOR

CROSS-REFERENCE TO RELATED APPLICATION

This application claims priority to U.S. Provisional Patent Application Ser. No. 62/453,700, filed on Feb. 2, 2017, and entitled UNPRESSURIZED CALIBRATION GAS TEST DEVICE, which is hereby incorporated by reference in its entirety.

FIELD

This disclosure is generally related to a device and method for testing a gas detector and more specifically to a device and method that utilize an unpressurized gas-releasing cartridge to generate a test gas.

BACKGROUND

Gas detectors are used widely in industrial settings where the presence of particular gases in the environment must be monitored. For example, within a petroleum refinery, gas detectors are utilized to check for leaks of chemicals being used in the refining process into the environment of the production facility.

Gas detectors are sensitive pieces of equipment. The detectors are periodically tested to make sure that the detector accurately monitors when a particular concentration of the gas being tested is present.

The majority of gas detectors are tested with a pressurized gas vessel or cylinder and regulator arrangement, wherein the gas to be tested for is provided from the high pressure gas cylinder at high pressure to a step down pressure regulator and from there by means of attached tubing to the gas detector, which is necessary since the vast majority of gas detectors are not built to withstand high pressure. Such gas cylinders are highly regulated as Dangerous Goods because of their pressure. In particular, shipment of such a pressurized vessel must be performed by a licensed carrier to ensure that safety protocols are followed to avoid accidents with the pressurized vessels.

SUMMARY

In one aspect, a test device for testing a gas detector comprises a cavity and a storage medium in the cavity that stores detectable gas. A calibrated orifice releases the detectable gas from the cavity. An air inlet provides air that is mixed with the detectable gas to form a proportioned mixture of air and detectable gas. An outlet is configured to provide the proportioned mixture to a gas detector.

In another aspect, a test device for a gas detector configured to detect a detectable gas comprises a receptacle defining a chamber for receiving therein a replaceable gas-releasing cartridge configured to release the detectable gas. An interface is configured for fluidly coupling the test device to the gas detector such that gas is deliverable through the interface to the gas detector. Passaging is configured to provide fluid communication between the interface and both a gas-releasing cartridge received in the chamber and an external environment of the test device. A pump is configured to pump air from the external environment and the detectable gas released from the gas-releasing cartridge received in the chamber through the passaging such that the pumped detectable gas and air form a proportioned mixture for testing the gas detector. The pump is configured to pump the proportioned mixture through the interface to the gas detector.

In still another aspect, a method of testing a gas detector configured for detecting a detectable gas comprises releasing the detectable gas from a gas-releasing cartridge by desorbing the detectable gas from a desorption substrate. The detectable gas is delivered to the gas detector.

In yet another aspect, a cartridge for delivering a detectable gas to a gas detector comprises a container defining a cavity and an outlet opening. The outlet opening is configured to be fluidly coupled to the gas detector. A storage medium is received in the cavity. Detectable gas is stored in the storage medium such that the detectable gas is configured to be desorbed from the storage medium.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
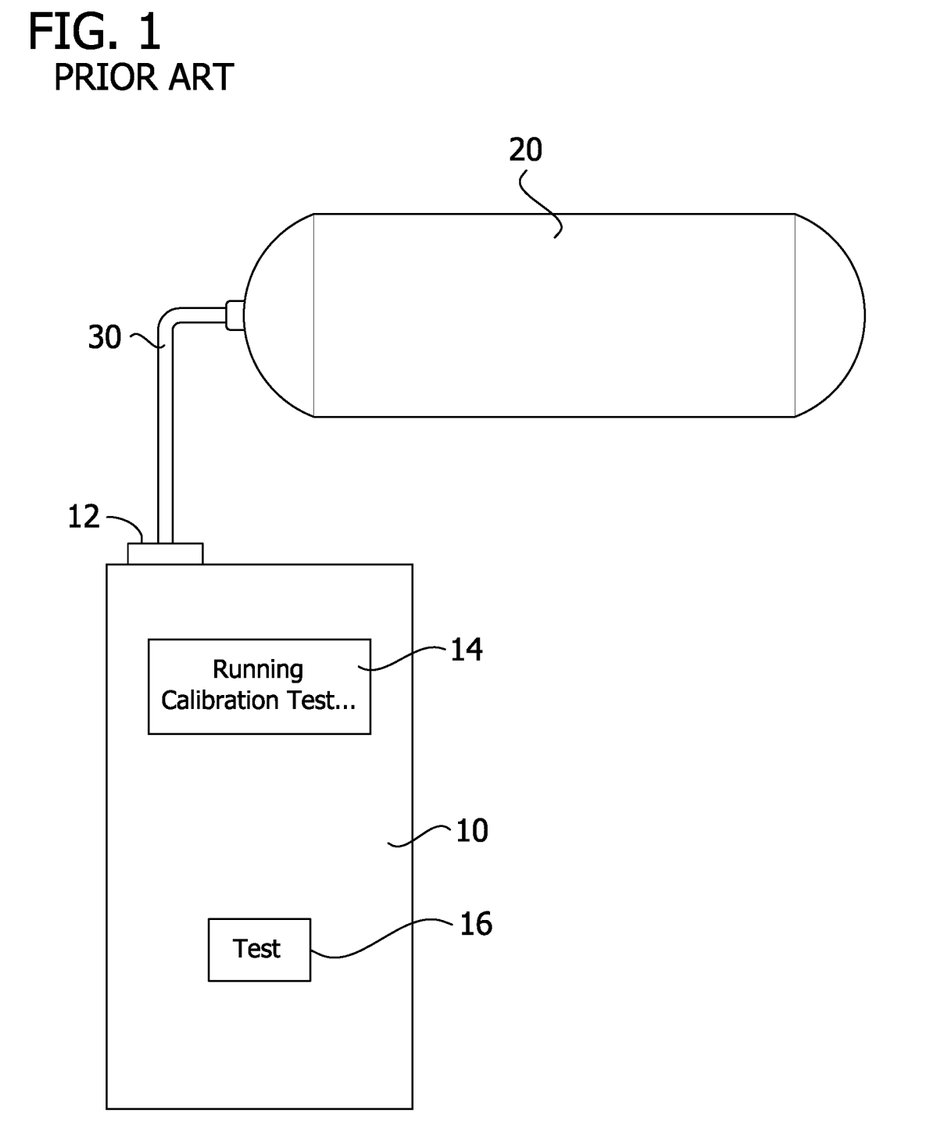
FIG. 1 is a schematic illustration of a prior art gas detector test configuration including a gas detector coupled to a pressurized test device.

Referring to FIG. 1, a gas detector is generally indicated at reference number 10. The gas detector 10 is connected to a pressurized gas vessel 20. The vessel 20 is configured to discharge a test gas including a detectable gas that the gas detector 10 is configured to detect and a balance of fill gas. The detectable gas and the balance of fill gas are delivered as a mixture from the vessel 20 to the detector 10. The vessel 20 is a gas cylinder, configured to contain pressurized gas at high pressure. In certain embodiments, the cylinder 20 also includes a regulator (not shown) that regulates the flow of gases from the cylinder to the detector 10. One having skill in the art will appreciate that the pressurized gas in the vessel 20 is a safety risk. If the vessel 20 is dropped, pierced, or otherwise mistreated, the high pressure gas can be explosively released.

The gas detector 10 includes pump inlet 12 through which gas is received into detector 10. The detector 10 further includes a display window 14 and a test activation button 16. Gas detectors come in various configurations and include various input and output mechanisms, and detector 10 is provided as a non-limiting example. A gas discharge tube 30 fluidly connects the vessel 20 to the inlet 12 to deliver test gas from the vessel to the detector 10.

Figure 2:
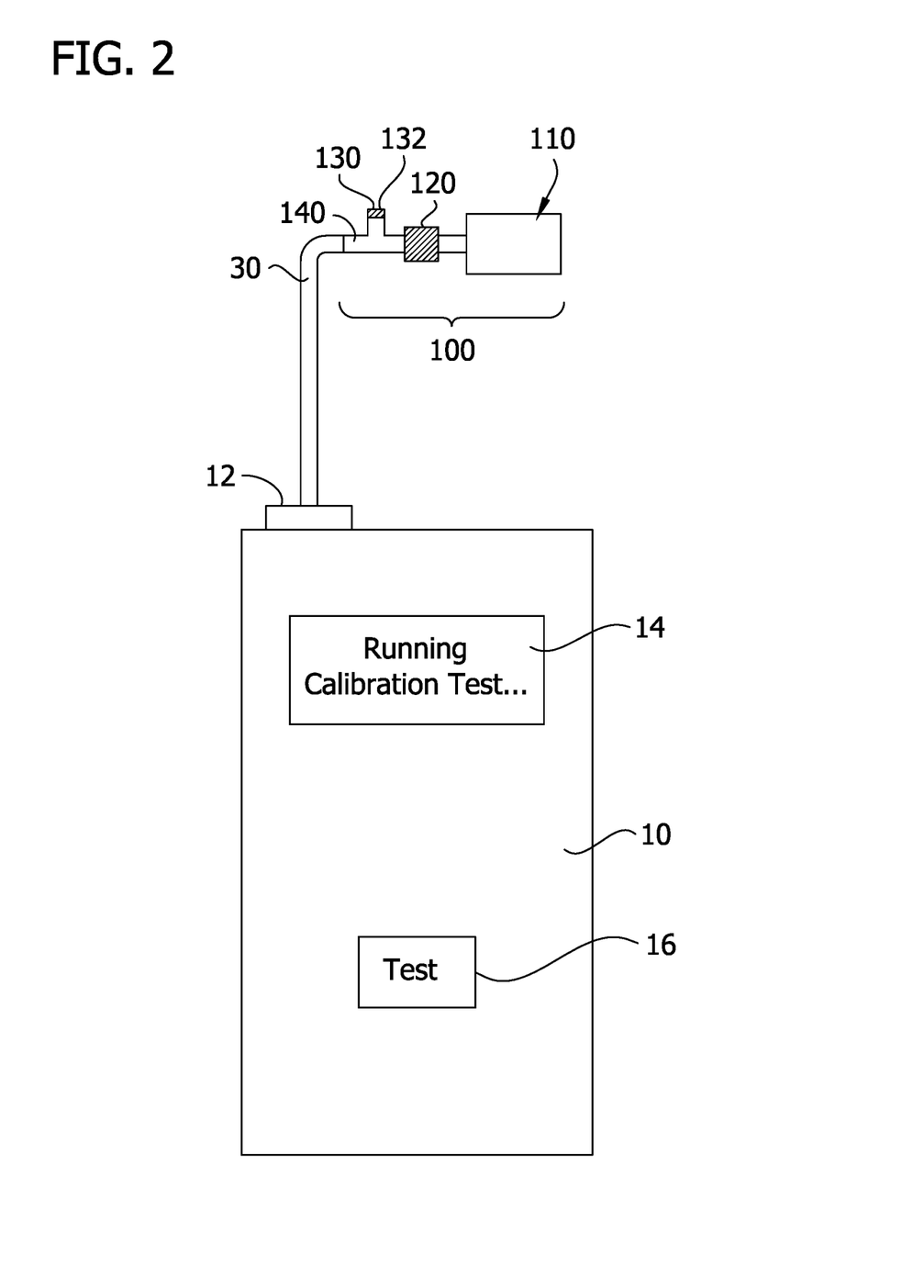
FIG. 2 is a schematic illustration of an unpressurized test device operatively connected to the gas detector of FIG. 1.

Referring to FIG. 2, an unpressurized test device for testing the gas detector 10 is generally indicated at 100. The illustrated test device 100 includes a gas-releasing cartridge 110, a calibrated orifice 120, an ambient air inlet 130, and an outlet 140.

The cartridge 110 includes a storage medium 116 (FIG. 3) that stores a quantity of detectable gas. For example, detectable gas can be absorbed or adsorbed into a substrate of the storage medium 116. In one exemplary embodiment, the cartridge 110 can comprise a carbon substrate that stores the detectable gas. Testing has shown that such a storage medium 116 can slowly release the detectable gas over time at a predictable and nearly constant rate. The cartridge 110 is configured to release the detectable gas from the storage medium 116. Referring to FIG. 2, a calibrated orifice 120 is fluidly coupled to the cartridge 110 to receive the detectable gas released from the cartridge 110. The detectable gas discharged from the cartridge 110 is deliverable through the calibrated orifice. Because the storage medium 116 releases the detectable gas at a predictable and nearly constant rate, selection of a calibrated orifice with a particular orifice diameter will provide a predictable and calibrated flow rate of detectable gas through the orifice.

In the illustrated test device 100, the storage medium 116 is configured to release the detectable gas. As a result, a pressurized gas vessel is not needed to test the detector 10. Moreover, the cost and safety issues associated with keeping pressurized gas vessels is eliminated through use of the test device 100.

The calibrated orifice 120 is connected to passaging comprising a tee fitting, which includes a lateral ambient air inlet 130. The lateral air inlet 130 is also sized and arranged to define an orifice that is calibrated to allow air to pass into the test device 100 through the lateral air inlet at a predetermined flow rate. The ambient air inlet 130 can include a filter cap 132 to keep out contaminants. Ambient air drawn in through inlet 130 mixes with the detectable gas flowing through the orifice 120. The air and the detectable gas mix to form a proportioned mixture that is discharged from the device 100 through the outlet 140. The outlet 140 (e.g., an interface) is connected to the gas discharge tube 30 which is connected to the inlet 12 of the gas detector 10.

The gas detector 10 includes pump inlet 12 through which gas flows into the detector 10. The detector 10 further includes a display 14 and a test activation button 16 (broadly, a switch). The gas detector 10 can include a pump configured to draw air through the inlet 12. The gas detector 10 can also be a passive unit (e.g., operate without a pump), simply permitting ambient air to flow in through the inlet 12.

Figure 3:
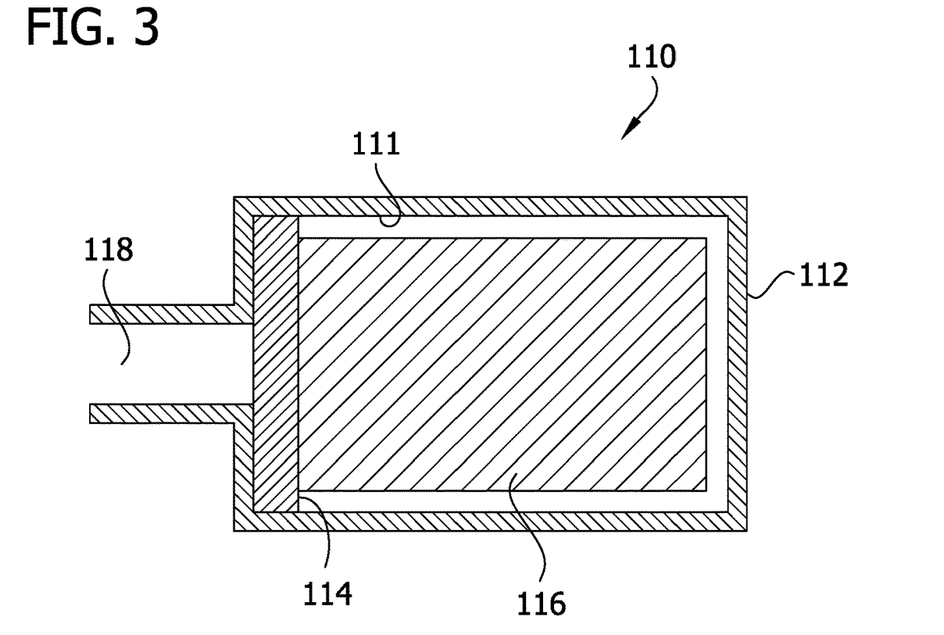
FIG. 3 is a schematic illustration of a gas-releasing cartridge of the test device of FIG. 2.

Referring to FIG. 3, the cartridge 110 includes a container 112 defining a cavity 111 for receiving the storage medium 116, a plain restraining filter 114, and an outlet 118 in fluid communication with the cavity 111. In one embodiment, the only opening through the container 112 is the outlet 118. As explained above, the cartridge 116 can include a carbon substrate or similar medium (e.g., clathrates) which, when exposed to a flow of the detectable gas, can store (e.g., absorb or adsorb) the detectable gas.

Figure 4:
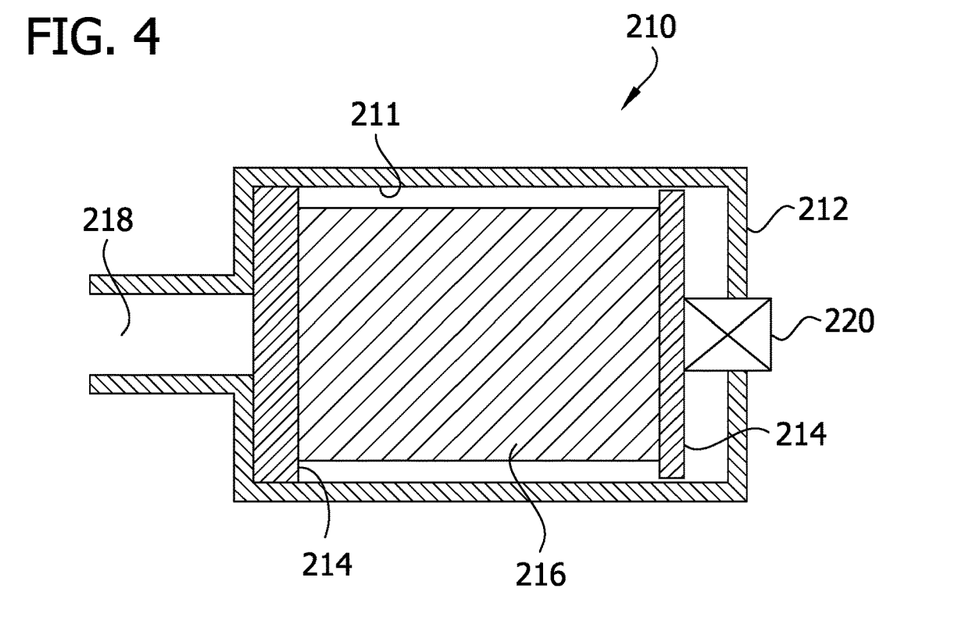
FIG. 4 is a schematic illustration of another embodiment of a gas-releasing cartridge.

Referring to FIG. 4, another embodiment of a cartridge that can be used with the test device 100 is generally indicated at reference number 210. The cartridge 210 is similar to the cartridge 110, except that the cartridge 210 includes an inlet orifice or inlet valve 220 that permits air to flow into the cavity 211. The orifice or valve 220 can be shut or capped when the test device 100 is not in use. Like the cartridge 110, the cartridge 210 includes a container 212 that defines a cavity 211 and a gas-releasing cartridge 216 inside the cavity. The cartridge 210 includes two plain restraining filters 214, one covering the inlet 220 and the other covering the outlet 218.

Figure 5:
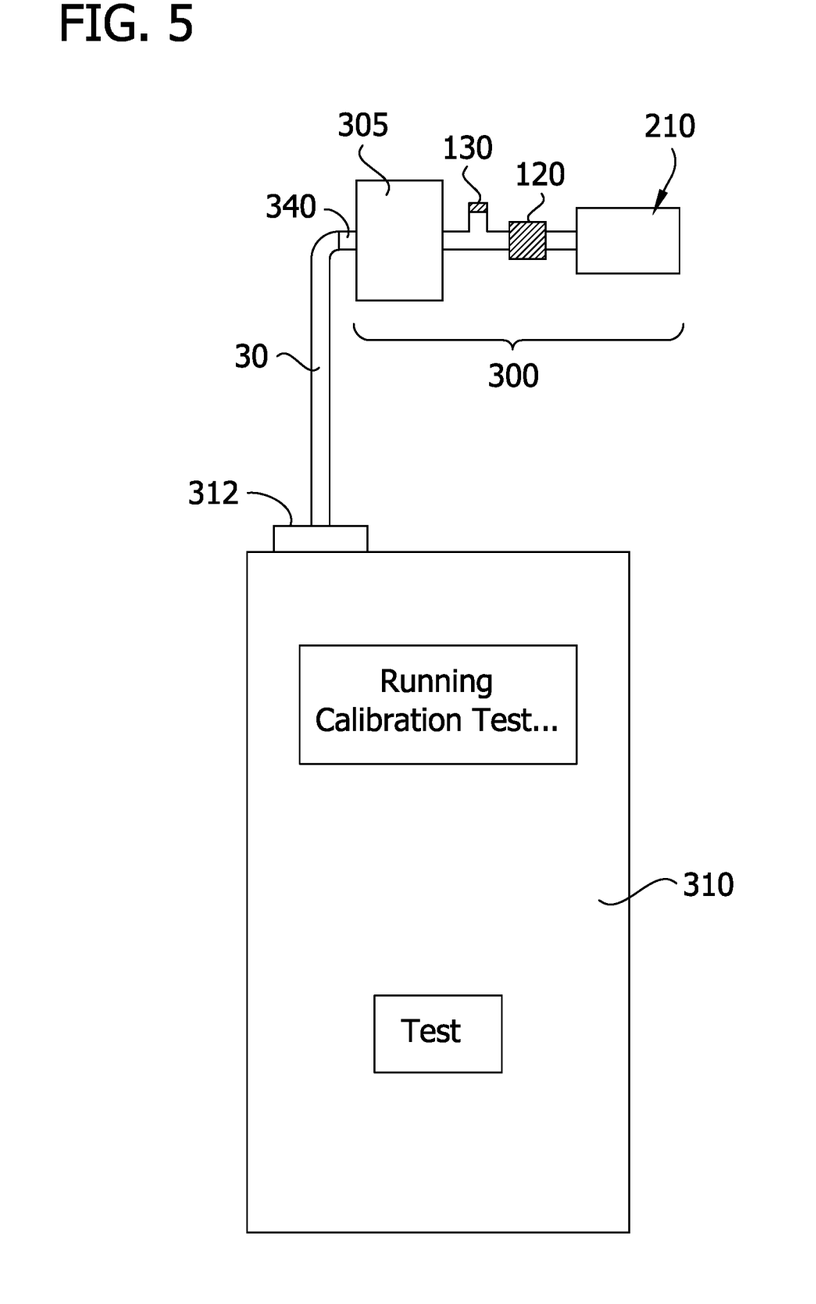
FIG. 5 is a schematic illustration of another embodiment of a gas detector coupled to another embodiment of an unpressurized test device incorporating the gas-releasing cartridge of FIG. 4.

Referring to FIG. 5, another embodiment of a test device for testing a gas detector 10 is generally indicated at reference number 300. The test device 300 includes the cartridge 210, the calibrated orifice 120, and the ambient air inlet 130 described above. In addition, the test device 300 includes a pump 305. The pump 305 is powered, either through A/C power or battery power. The pump 305 is configured to draw air into the cavity 211 of the cartridge 210 through the inlet 220 and to draw air into the air inlet 130. The pump pumps proportioned amounts of the air and detectable gas generated by the cartridge through the discharge tube 30 to a gas detector 310. As the air and detectable gas are pumped by the pump, the gases are thoroughly mixed to form a proportioned mixture.

The gas detector 310 has gas inlet 312. The gas detector 310 is a passive gas detector, which does not include a pump for drawing air through inlet 312. The pump 305 of the device 300 can pump the desired proportioned mixture of air and detectable gas to detector 310.

Figure 6:
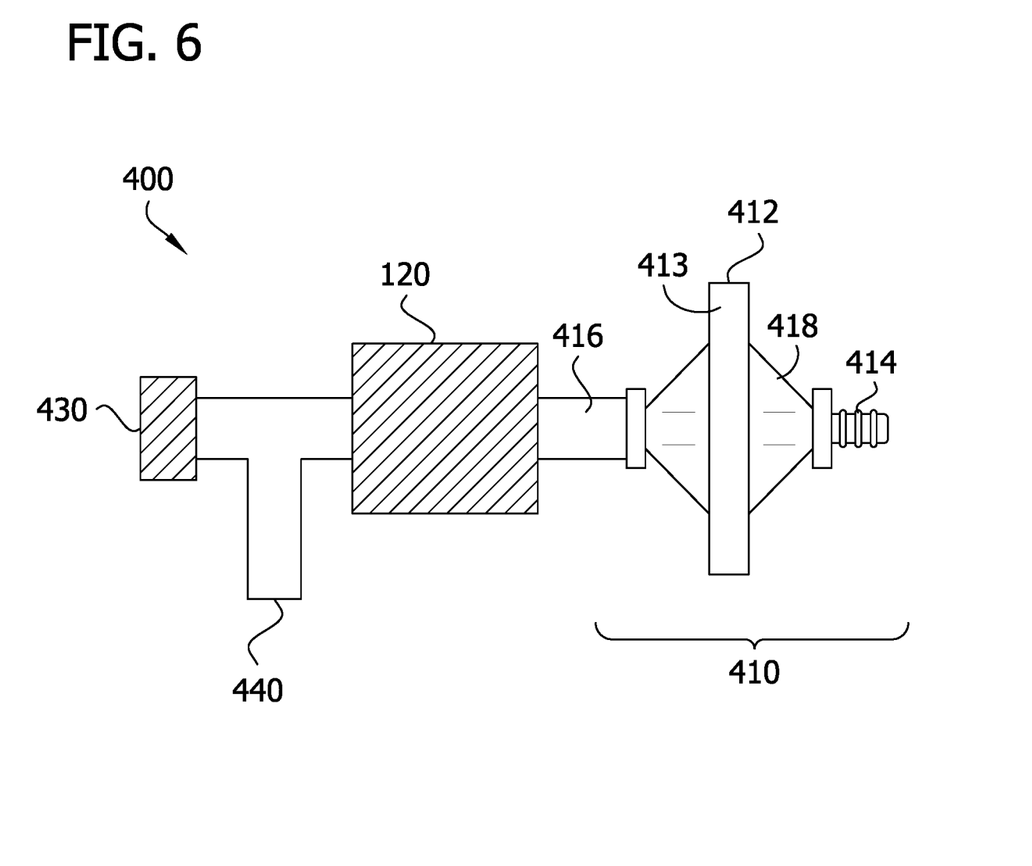
FIG. 6 is a schematic illustration of another embodiment of an unpressurized test device.

Referring to FIG. 6, another embodiment of a test device for testing a gas detector 10, 310 is generally indicated at reference number 400. The illustrated test device 400 includes a cartridge 410 comprising a disc filter 413 contained within a disc filter housing 412. Disc filters are known in the art and used in gas lines to filter the flow of a gas. Disc filter 413 acts as storage medium for detectable gas (e.g., a substrate) in accordance with the present disclosure, e.g., the detectable gas is initially stored in the filter. The disc filter housing 412 includes an inlet 414 for drawing ambient air into the cartridge 410, an outlet 416, and reinforcement ribs 418. A number of disc filters and disc filter housings are known in the art, and any can be used that can be configured to release the detectable gas stored in the filter at a predictable rate.

The test device 400 further includes a calibrated orifice 120, an ambient inlet 430 including a filter, and an outlet 440 configured to be fluidly connected to a gas detector 10, 310. Although the illustrated embodiment includes an ambient inlet 430 that is in-line with the disc filter housing 412 and an outlet 440 that extends laterally, in other embodiments the ambient inlet forms a lateral port and the outlet is in line with the disc filter housing 412. Still other configurations are possible within the scope of the present invention.

A non-limiting example of a test device 100 used with the gas-releasing cartridge 210 will now be described. In the example, the test device 100 is configured to deliver a proportioned mixture of about 100 ppm isobutylene and air to a gas detector 10.

In this example, a container 212 is packed with activated carbon or other suitable adsorbent (broadly, substrate material). Activated carbon is adsorbent material for a wide variety of gases and thus provides a suitable substrate material for many types of gases, including isobutylene. Isobutylene is directed into contact with the activated carbon (before or after it is placed in the container 212) and is thereby adsorbed by the activated carbon. Other substrates such as silica gel and zeolitic materials can also be used for certain gases. Silica gel may, for example, be a preferable substrate material for storing detectable gases containing moisture. Zeolites may, for example, be a preferable substrate material for storing ammonia.

In the instant isobutylene example, an activated carbon storage medium 216 storing the isobutylene is placed in a container 212 to form a gas-releasing cartridge 110. A tee fitting 140 is attached to the outlet 218 of the cartridge 210, as illustrated in FIG. 2.

The tee fitting 140 is attached via a short tube connector 30 to the inlet 12 of the gas detector 10.

The pump in the gas detector 10 draws ambient air into the test device 100 through the ambient air inlets 130, 220. The pump also creates a vacuum in the cavity 211 of the cartridge 210. The vacuum desorbs isobutylene from the activated carbon substrate. The desorbed isobutylene mixes with the air being drawn into the test device 100 to form a proportioned mixture of isobutylene and air. Varying the amount of air pulled through air inlets 130, 220 (as non-limiting examples, by either controlling the size of their orifices or by slowing the amount of air taken in by impeding them with filters) varies the concentration of isobutylene in the proportioned mixture. One of the air inlets 130, 220 can also be closed to create higher concentrations of isobutylene mixtures.

The filters 132, 214 remove unwanted contaminants from the air being drawn through the test device 100. To create multi-component gas mixtures, several of cartridges can be coupled together using a manifold then blended through one common orifice. For example, a mixture of isobutylene and hydrogen sulfide can be formed by using two cartridges coupled together by a common manifold. In this embodiment, the test device would create a proportioned mixture of hydrogen sulfide, isobutylene and air. Other variants are also possible.

In one embodiment, water is adsorbed onto a silica gel storage medium inside a cartridge. When air is pulled through this cartridge, a test device can create a proportioned mixture of water and air.

If the device is to be used for a gas detector without an integral pump, an external pump can be added to the test device to drive gas flow through the test device.

A test device can also be specially configured to account for other factors that can affect the proportions of detectable gas an air being drawn through the device. For example, orifice adaptors can be used to compensate for the unusual temperatures, etc. Unusual temperatures can affect desorption from a storage medium and a orifice adaptor can be used to compensate for change in the rate at which detectable gas is desorbed from the storage medium.

By testing, screens and/or filters can also be installed at the ports of a test device to create the desired flow conditions within the device.

In another embodiment, a micro ultrasonic transducer is used to encourage the release of the detectable gas from the storage medium.

In certain embodiments, adjustable valves (e.g., electric valves) can be used to adjust an orifice size to maintain the desired proportions of fluid components flowing through the test device under changing conditions (e.g., changing temperature conditions).

Figure 7:
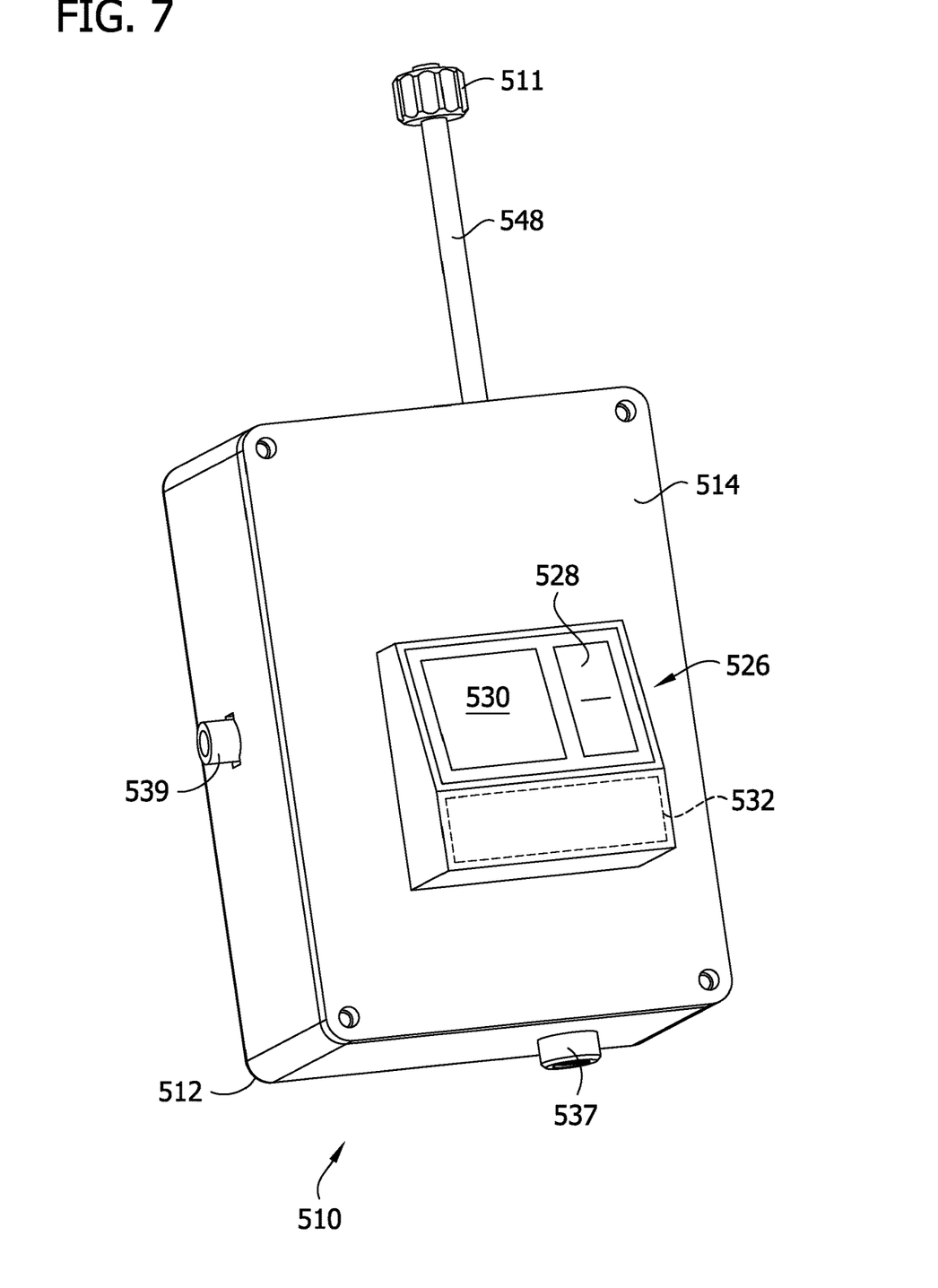
FIG. 7 is a perspective of another embodiment of a test device, schematically illustrating features of a control panel of the test device.
Figure 8:
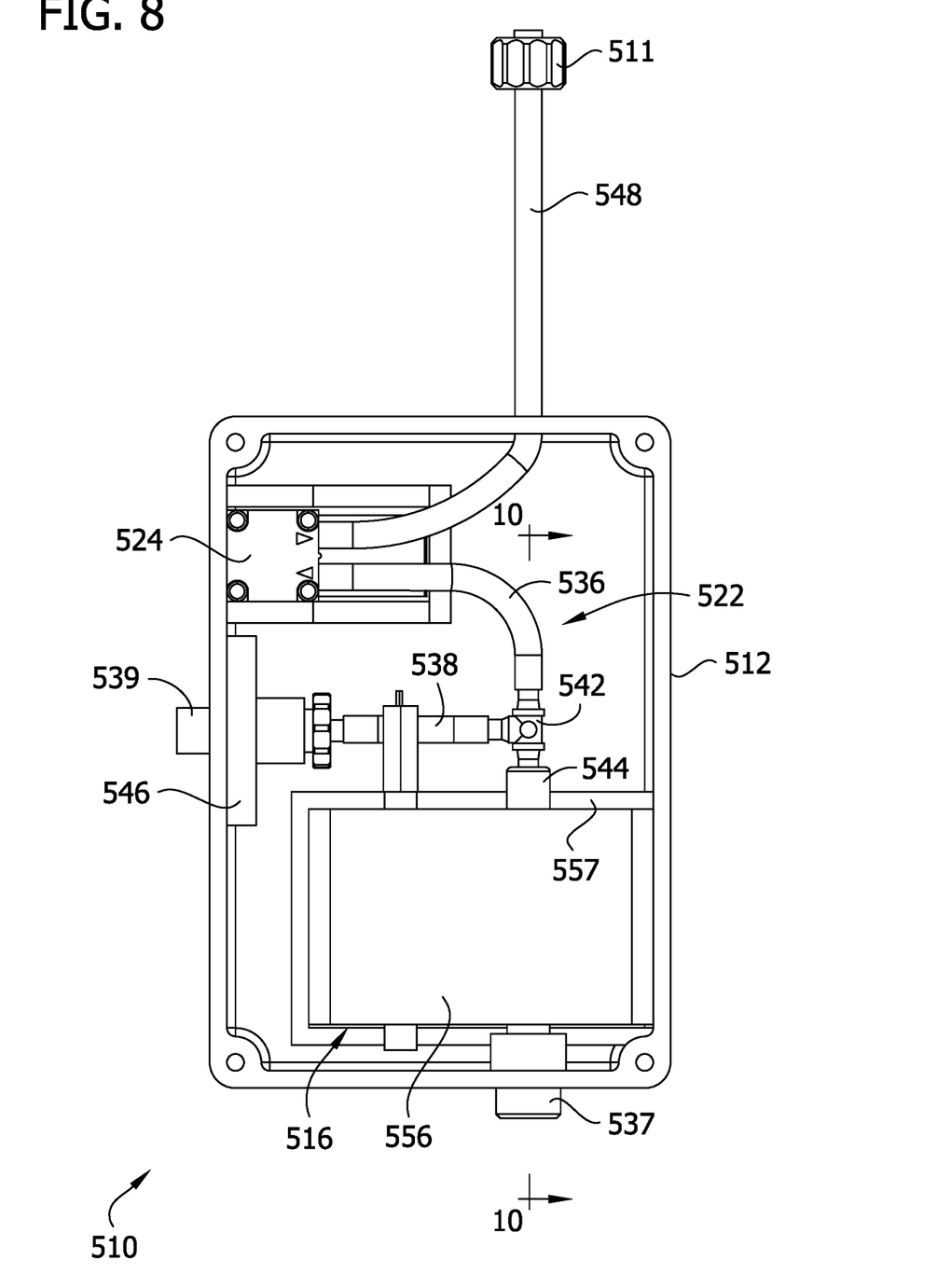
FIG. 8 is a front elevation of the test device of FIG. 7 with an access cover of the test device removed to reveal an interior of the test device.

Referring to FIGS. 7 and 8, another embodiment of a test device for testing a gas detector 10, 310 is generally indicated at reference number 510. The test device 510 includes an interface 511 for fluidly coupling the test device to the gas detector 10, 310. The test device 510 is generally configured to deliver a proportioned mixture of air and detectable gas through the interface 511 to the gas detector 10, 310 to, for example, determine whether the gas detector is accurately detecting the detectable gas and/or to calibrate the gas detector.

Figure 10:
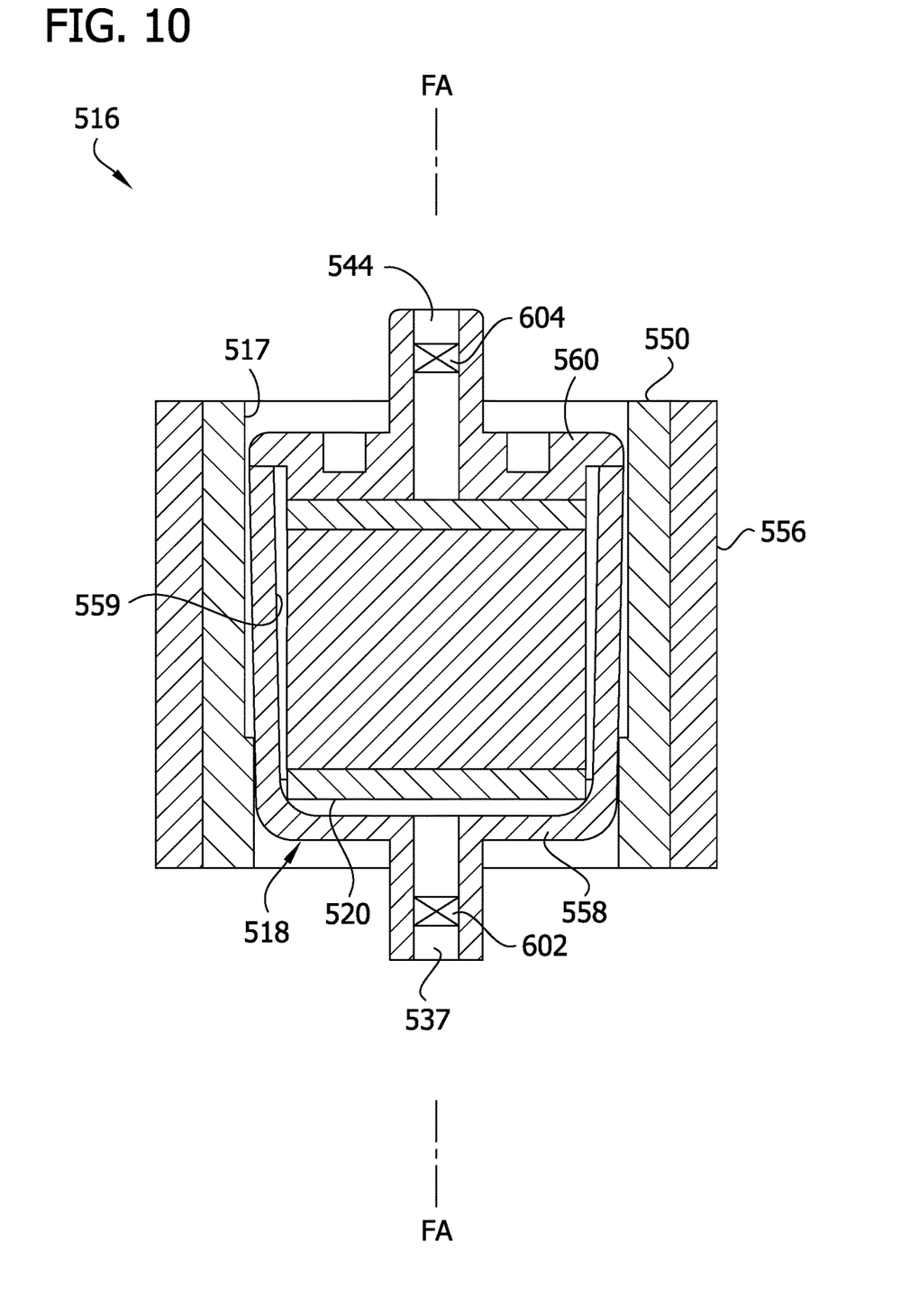
FIG. 10 is a cross-section taken in the plane of the receptacle indicated at line 10-10 of FIG. 8.

The test device 510 comprises a housing, generally indicated at 512, which includes an access cover 514 that can be removed (as in FIG. 8) to provide access to the interior of the housing. Inside the interior, the housing 512 supports a receptacle, generally indicated at 516, which defines a chamber 517 (FIG. 10) for receiving a replaceable gas-releasing cartridge, generally indicated at 518 (FIG. 10). As explained in further detail below, the gas-releasing cartridge 518 comprises a storage medium 520 that is configured to release a detectable gas that is detectable by the gas detector 510 (e.g., a "detectable gas"). As further described below, the housing 512 also supports passaging, generally indicated at 522 (FIG. 8), which provides fluid communication between the cartridge 518, the interface 511, and an external environment of the test device 510. A pump 524 (FIG. 10) is further supported in the interior of the housing 512. As explained below, the pump 524 is configured to pump air from the external environment and gas released from the cartridge 518 through the passaging 522 and the interface 511 to the test device.

Referring to FIG. 7, a control panel, generally indicated at 526, is supported on the access cover 514 for controlling the test device 510. The illustrated control panel 526 includes a switch 528 and a display 530. The switch 528 is configured for selectively actuating the test device to deliver a proportioned mixture of air and detectable gas to a gas detector 10, 310. In the illustrated embodiment, the switch 528 is operatively connected to a controller 532 that automatically controls certain functions of the test device. For example, the controller 532 is configured to control the pump 524 and certain controllable features of the receptacle 516, as described in greater detail below. In addition, the illustrated controller 532 is configured to control the display 530. In the illustrated embodiment, the display 530 can function as an indicator for indicating when the test device 510 is ready to deliver a proportioned mixture of air and detectable gas to a gas detector 10, 310. Other types of indicators (e.g., light panels, audio alarms, etc.) can also be used for the same purpose or other purposes in other embodiments. Although the illustrated embodiment uses a single controller 532 to control multiple aspects of the test device 510, it will be understood that other embodiments could use other control arrangements (e.g., more than one controller) without departing from the scope of the invention. In one or more embodiments, the test device 510 is powered by an external power source that is connected to the test device by a power cord (not shown). In other embodiments, the test device 510 could include an onboard power supply (e.g., a battery; not shown).

Referring to FIG. 8, the passaging 522 is configured to provide fluid communication between the interface 511 and both the cartridge 518 in the receptacle 516 and an external environment of the test device 510. In the illustrated embodiment, the passaging 522 includes a main intake tube 536 that defines a main intake passage extending between the cartridge 518 and an intake end of the pump 524. The pump is configured to draw detectable gas that is released from the cartridge 518 through the main intake tube 536. As will be explained in further detail below, the cartridge 518 provides fluid communication between the main intake tube 536 and a primary air inlet 537 that is in fluid communication with the external environment of the test device 510. Thus, as the pump 524 draws detectable gas from the cartridge 518 into the main intake tube 536, it also draws air through the inlet 537 into the cartridge and the main intake tube.

In the illustrated embodiment, the passaging 522 further includes a secondary intake tube 538 that defines a secondary intake passage. The secondary intake passage extends laterally from the main intake passage to a secondary air inlet 539. In one or more embodiments, the secondary air inlet 539 includes an orifice that is sized to calibrate the flow of air into the passaging through the orifice in proportion to the rate at which detectable gas is released from the cartridge 518. In the illustrated embodiment, a tee fitting 542 connects the secondary intake tube 538 to the main intake tube 536. A main portion of the tee fitting 542 extends between an outlet 544 of the cartridge 518 and the main intake tube 522, and a lateral portion of the tee fitting is connected to the secondary intake tube 538. An air filter 546 extends across the secondary air inlet 539 to filter air that enters the test device 510 through the secondary air inlet. It is understood that another air filter (not shown) could likewise be used to filter air that enters the test device through the primary air inlet 537. The pump 524 is configured to draw air from the external environment in series through the secondary air inlet 539, the filter 546, the secondary intake tube 538, and the tee fitting 542 into the main tube 536. In the illustrated embodiment, the intake tubes 536, 538 comprise flexible hoses that can be moved out of the way when the cartridge 518 is being replaced. It will be understood that, in certain embodiments, the passaging will have only one air intake passage or more than two air intake passages. For example, it is contemplated that the primary air inlet 537 or the secondary air intake tube 538 could be omitted from the test device 510.

The passaging 522 also includes a discharge tube 548, which can also comprise a flexible hose in certain embodiments. The discharge tube 522 defines a discharge passage that extends from a discharge end of the pump 524, through a wall of the housing 512, to the gas detector interface 511. The pump 524 delivers air and detectable gas from the main intake tube 536 through the discharge tube 548 and the interface 511 to the gas detector 10, 310. As the pump 524 pumps air and detectable gas through the main intake passage and the discharge passage, the fluids are mixed together.

The test device 10 is configured so that the flow rate at which the pump 524 draws air into the passaging 522 is proportional to the rate at which detectable gas is released from the storage medium 520. Accordingly, the test device 10 is configured to form a proportioned mixture having the required concentration of detectable gas for testing the gas detector 10, 310. More specifically, the flow rate at which the pump 524 draws air through the passaging 522 is generally calibrated to the rate at which the storage medium 520 releases the detectable gas during use. Calibrating the rate at which the pump 52 draws air into the passaging 522 involves, for example, sizing the inlets 537, 539, the cartridge 518, and/or the passages of the tubes 536, 538, 548 based on the power of the pump 524. These variables are adjusted in accordance with an expected rate at which detectable gas will be released from the storage medium 520 during use to achieve the air flow rate for producing a proportioned mixture that has the required concentration of detectable gas. It is understood that, if a balance of fill gas other than environmental air is desired, the inlets 537, 539 could be coupled to an alternative source of balance of fill gas.

Figure 9:
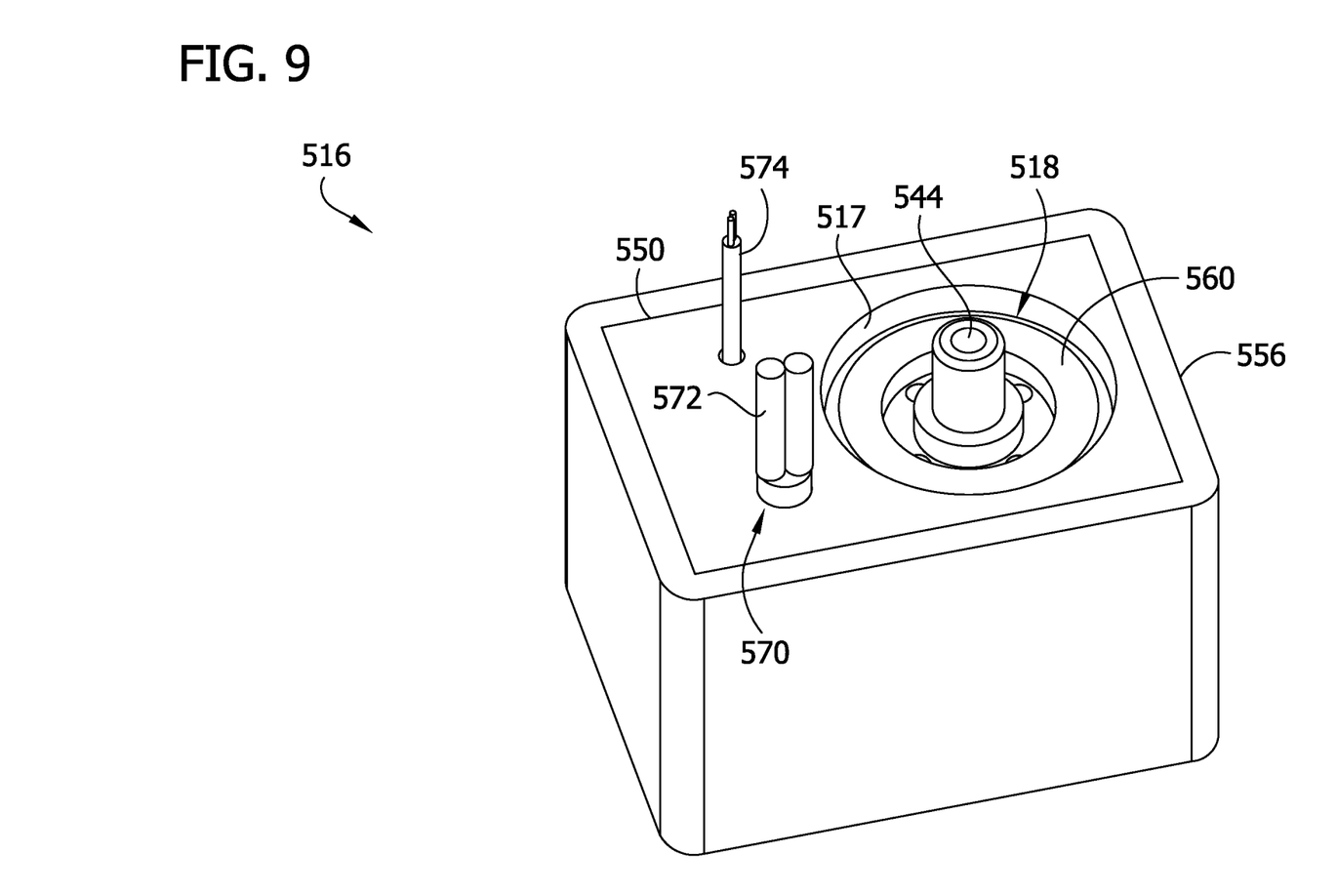
FIG. 9 is a perspective of a receptacle of the test device of FIG. 7.

Referring to FIGS. 9 and 10, the receptacle 516 includes a generally rectangular block 550 that defines a cylindrical chamber 517 extending from a top through a bottom of the block. In one or more embodiments, the block 550 is formed of thermally conductive material (e.g., a metal such as aluminum or copper). In the illustrated embodiment, the receptacle 516 includes a thermally insulating jacket 556 that extends around a perimeter of the thermally conductive block 550. As shown in FIG. 8, the block 550 and jacket 556 are received in a fitted compartment 557 of the housing to secure the receptacle 516 in position inside the test device 510.

Referring to FIG. 10, the cartridge 518 is positioned in chamber 517 of the block 550. The cartridge 518 comprises a container 558 that defines a cavity 559 for receiving the gas-releasing storage medium 520 therein. The illustrated container 558 includes a generally cylindrical side wall and a bottom wall. The top of the cylindrical side wall is open. A tube extends downward from the bottom wall of the container 558 and defines the primary air inlet 537, which provides fluid communication between the cavity 518 and the external environment of the test device 510. In the illustrated embodiment, the cartridge includes a valve 602 (illustrated schematically in FIG. 10) that is fluidly coupled to the primary air inlet 537. The valve 602 is constructed to remain closed (e.g., close the inlet 537) until the cartridge is installed in the testing device 510. In one or more embodiments, the container 558 is thermally coupled to the conductive block 550 such that heat is conducted through the block and the container to the cavity 559. The container 558 can comprise a thermally conductive material to enhance heat transfer between the block 550 and the storage medium 520 inside the cavity 559. A cap 560 extends over the open top end of the container 558 and defines the top of the cavity 559. The cap 560 includes a tube that extends upward and defines the fluid outlet 544 of the cartridge 518, which is in fluid communication with the cavity 559. As shown in FIG. 8, the tee fitting 542 is fluidly coupled to the outlet 544 to provide fluid communication between the outlet of the cavity 559 and the passaging 522. The cartridge includes a valve 604 (illustrated schematically in FIG. 10) that is fluidly coupled to the outlet 544. The valve 604 is constructed to remain closed (e.g., close the outlet 544) until the cartridge is installed in the testing device 510. In some embodiments, the valves 602, 604 or either of them can be controlled by the testing device 510 to open and close.

In the illustrated embodiment, the inlet 537 and the outlet 544 of the cartridge 518 are aligned along a common flow axis FA. During use, air flows into the cavity 559 along the flow axis FA through the inlet 537. The air flows generally along the flow axis FA through the cavity 559 and mixes with detectable gas being released by the cartridge 518. The air and detectable gas subsequently flow along the flow axis FA through the outlet 544 into the passaging 522. Although other flow arrangements can be used without departing from the scope of the invention, as will be explained below, the axial flow path from the inlet 537 through the outlet 544 is thought to enhance consistency and predictability of the detectable gas concentration in the proportioned mixture that the test device 510 produces.

In the illustrated embodiment, the container 558, the storage medium 520, and the cap 560 are all components of a disposable cartridge 518. When the storage medium 520 becomes spent and is no longer capable of releasing detectable gas as required for testing the gas detector 10, 310, a user can remove the access cover 514 of the test device 510 to access the receptacle 516. After removing the access cover 514, the passaging 522 is disconnected from the outlet tube 544 of the spent cartridge 518. The container 558, the storage 520, and the cap 560 are removed as a unit from the chamber 517. After the spent cartridge 518 assembly is removed, it is replaced with a new cartridge. The new cartridge 518 is placed in the chamber 517 and fluidly coupled to the passaging 522, and the access cover 514 is replaced. It is contemplated that in other embodiments, that the spent storage medium 520 is replaceable and one or both of the container 558 and the cap 560 are reused. In addition, the cartridge 518 may be insertable and removable from the receptacle 516 in other ways, such as without having to remove the access cover 514.

In one or more embodiments, the storage medium 520 comprises a desorption substrate that stores the detectable gas. For example, the detectable gas can be absorbed or adsorbed in the desorption substrate. The storage medium 520 is configured so that the detectable gas is desorbed from the desorption substrate when the desorption substrate is heated. In certain embodiments, the desorption substrate can comprise an activated charcoal. In other embodiments, the desorption substrate can comprise a silica and/or a clathrate. Still other desorption substrates can be used without departing from the scope of the invention. In the illustrated embodiment, the desorption substrate is porous to allow air flow through the cartridge 518 along the axis FA. Any gas that is detectable by a gas detector can be included in the storage medium 520 to be desorbed from the desorption substrate. For example, in certain embodiments, the storage medium 520 can comprise a desorption substrate and a detectable gas such as one or more of a freon, hydrocarbon, nitrous oxide, propane, hydrogen sulfide, carbon dioxide, methane, ethylene, chlorine, ammonia, sulfur dioxide, butane, ethane, pentane, hexane, hydrogen chloride, R407C, R134a, another refrigerant gas, ethylene oxide, toluene, benzene, chloroform, another liquefied gas with a vapor head, etc.

As In certain embodiments, the storage medium comprises loose material that is packed into the cavity 559. Suitably, the loose material is packed into the container 558 such that it substantially fills the cavity 559 but defines void space through which air and detectable gas can flow through the storage medium 520 to the outlet 544. For example, in one embodiment the storage medium 520 comprises granular material that is packed into the container 558 such that void space between discrete pieces of material defines at least one gas flow path (e.g., an interconnected network of gas flow paths) that extends between the primary air inlet 537 and the outlet 544. In certain embodiments, the void space provides fluid communication between the inlet 537 and the outlet 544. In one embodiment, the storage medium has a porosity in an inclusive range of from about 1% to about 20% (e.g., from about 3% to about 5%). In the illustrated embodiment, the volume of the mass is substantially equal to the volume of the cavity 559. A storage medium having a relatively low but non-zero porosity has been found to provide consistent and predictable desorption of detectable gas during use.

Referring to FIG. 9, the illustrated receptacle comprises a heating system 570 that is configured to heat the cartridge 518 to an elevated temperature so that detectable gas is desorbed from the desorption substrate. The heating system 570 includes a heater 572 that is thermally coupled to the conductive block 550. The block 550 conducts heat from the heater 572 to the container 558, which transfers heat to the storage medium 520. Any suitable heater for heating a thermally conductive block can be used without departing from the scope of the invention. The heating system 570 further comprises a temperature sensor 574 that is configured to generate a temperature signal that is representative of the temperature of the cartridge 518. In the illustrated embodiment, the temperature sensor 574 is received in a well formed in the block 550 and thus directly senses the temperature of the block, which is related to the temperature of the cartridge 518. The temperature sensor 574 provides a temperature signal to the controller 532, which thermostatically controls the heater 572 to maintain the cartridge 518 at a constant, elevated temperature for desorbing detectable gas from the storage medium 520

Referring to FIG. 7, a user activates the test device 510 using the switch 528. Initially, the controller 532 activates the heater 572. The controller 532 is also configured to execute a startup routine after the test device 510 is activated with the switch 528. During the startup routine, the controller 532 uses the heater to heat the cartridge 518 to an elevated temperature for desorbing the desorption gas. At the end of the startup routine, the controller 532 actuates the display 530 to provide a readiness indication indicating that the detectable gas is being released from the cartridge 518 at the rate for forming the proportioned mixture required for testing the gas detector 10, 310. In one embodiment, the controller 532 is configured to provide the readiness indication after the heater 572 has been active for a predetermined amount of time. In another embodiment, the controller 532 is configured to provide the readiness indication based on the temperature signal from the temperature sensor 574. The controller can control the display of the readiness indication in still other ways in other embodiments.

In certain embodiments, the controller 532 prevents the pump 524 from being activated during the startup routine. For example, in one embodiment, the controller 532 automatically activates the pump 524 when it displays the readiness indication on the display 530. In another embodiment, the controller 532 prevents the user from activating the pump 524 using the switch 528 during the startup routine and allows the user to activate the pump 524 using the switch 528 after the readiness indication is displayed on the display. The controller 532 can also be configured to prevent pump activation until the interface 511 of the test device 510 is properly coupled to the gas detector 10, 310. In another embodiment, during the startup routine or after the startup routine is complete, the controller 532 is configured to automatically activate the pump to purge the cavity 559 and passaging 522 before the test device 510 is connected to the gas detector 10, 310.

In general, testing a gas detector 10, 310 using the test device 510 comprises releasing a detectable gas from the cartridge 518 by desorbing the detectable gas from the desorption substrate and directing the released detectable gas to the gas detector. When the pump 524 is active and the test device 510 is properly coupled to the gas detector 10, 310, air is drawn into the test device through the inlets 537, 539 at a calibrated flow rate. Simultaneously, the heater 572 heats the cartridge 518 to an elevated temperature so that detectable gas is desorbed from the desorption substrate at an expected rate. Air flows along the flow axis FA through the inlet 537 into the cavity 559 and mixes with the desorbed detectable gas. The pump 524 draws the air and detectable gas from the cavity 559 along the flow axis FA through the outlet 544 and the tee fitting 542 into the main intake passage. Air from the secondary inlet 539 is also drawn through the secondary intake tube 538 and the tee fitting 542 into the main intake tube 536. The air and detectable gas mix to form the proportioned mixture as they flow through the main intake tube 536, the pump 524, and the discharge tube 548. The pump 524 delivers the proportioned mixture through the interface 511 to the gas detector 10, 310 while the gas detector is operating in a test mode. If the gas detector 10, 310 is operating properly, it will detect the detectable gas in the proportioned mixture and provide an indication. If the gas detector 10, 310 fails to detect the detectable gas, the user will understand that the detector is not operating properly. In another embodiment, the user uses the proportioned mixture (which has a known concentration of the detectable gas) to determine whether the gas detector 10, 310 is correctly registering the amount of detectable gas in the mixture. If the gas detector 10, 310 is registering the incorrect amount of detectable gas, the user can recalibrate the gas detector 10, 310 based on the known amount of detectable gas in the mixture being delivered to the detector.

The detectable gas stored in the storage medium 520 becomes spent after substantially all of the detectable gas is desorbed from the desorption substrate. In certain embodiments, the controller 532 can be configured to determine when a cartridge 518 is spent and display a spent cartridge indication on the display 530. For example, the controller 532 can determine that a cartridge 518 is spent when a predetermined number of tests are performed using the cartridge, after the cartridge has been heated by the heater 572 for a cumulative predetermined amount of time, after the pump 524 has been active with the cartridge loaded into the chamber 517 for a cumulative predetermined amount of time, etc. When the cartridge 518 is spent, the user can dispose of the spent cartridge and replace it with a new cartridge or cartridge assembly as described above.

As can be seen, the test device 510 can be used to test a gas detector 10, 310 without a pressurized canister. The test device 510 can be used at low pressures and without any valves. The rate at which detectable gas is released from the cartridge 518 can be predictably controlled by thermostatically heating the cartridge and limiting resorption of the detectable gas into the desorption substrate. Thus, the test device 510 can consistently deliver to a gas detector 10, 310 a proportioned mixture of air and detectable gas that has a concentration of detectable gas that is appropriate for testing the gas detector.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A test device for a gas detector configured to detect a detectable gas, the test device comprising:
    a receptacle defining a chamber for receiving therein a replaceable gas-releasing cartridge configured to release the detectable gas;
    an interface for fluidly coupling the test device to the gas detector such that gas is deliverable through the interface to the gas detector;
    passaging configured to provide fluid communication between the interface and both a gas-releasing cartridge received in the chamber and an external environment of the test device; and
    a pump configured to pump air from the external environment and the detectable gas released from the gas-releasing cartridge received in the chamber through the passaging such that the pumped detectable gas and air form a proportioned mixture for testing the gas detector, the pump being configured to pump the proportioned mixture through the interface to the gas detector;
    wherein the passaging includes a main intake passage extending between the cartridge received in the receptacle and the pump, and the passaging includes a secondary intake passage extending laterally from the main intake passage to a secondary air inlet.

2. A test device as set forth in claim 1, further comprising a heater configured to heat the gas-releasing cartridge received in the chamber.

3. A test device as set forth in claim 2, further comprising an indicator, the indicator being configured to be selectively actuated to provide an indication of when the detectable gas is being released from the gas-releasing cartridge at a rate for forming the proportioned mixture.

4. A test device as set forth in claim 3, further comprising an indicator controller configured to actuate the indicator after the heater has heated the gas-releasing cartridge for a predetermined amount of time.

5. A test device as set forth in claim 3, further comprising an indicator controller configured to actuate the indicator based on a temperature signal representative of a temperature of the gas-releasing cartridge.

6. A test device as set forth in claim 2, wherein the receptacle comprises a block formed from a thermally conductive material, the heater being configured to heat the gas-releasing cartridge received in the chamber by conducting heat through the block.

7. A test device as set forth in claim 1, wherein the passaging further comprises a discharge passage extending from the pump to the interface.

8. A test device as set forth in claim 1, further comprising the gas-releasing cartridge, the gas-releasing cartridge comprising a storage medium and the detectable gas stored in the storage medium, the storage medium being configured to release detectable gas.

9. A test device as set forth in claim 8, wherein the storage medium comprises a substrate material and the detectable gas is configured to be desorbed from the substrate material.

10. A test device as set forth in claim 9, wherein the gas-releasing cartridge is configured so that the detectable gas is desorbed from the substrate material when the desorption substrate is heated.

11. A test device as set forth in claim 9, wherein the substrate material comprises at least one of an activated charcoal, a silica, a zeolithic material, and a clathrate.

12. A test device as set forth in claim 9, wherein the gas-releasing cartridge further comprises a container defining a cavity receiving the storage medium therein.

13. A test device as set forth in claim 12, wherein the container defines an outlet opening configured to be fluidly coupled to the passaging.

14. A test device as set forth in claim 13, wherein the container further defines an inlet opening configured to provide fluid communication between the cavity and the external environment of the test device.

15. A test device as set forth in claim 8, wherein the storage medium has a porosity in an inclusive range of from about 1% to about 20%.

16. A test device as set forth in claim 15, wherein the storage medium has a porosity in an inclusive range of from about 3% to about 5%.

17. A cartridge for delivering a detectable gas to a gas detector, the cartridge comprising:
   a container defining a cavity and an outlet opening, the outlet opening being configured to be fluidly coupled to the gas detector, the container including an inlet port and an outlet port arranged to provide fluid communication with the cavity of the container;
   a storage medium received in the cavity; and
   detectable gas stored in the storage medium such that the detectable gas is configured to be desorbed from the storage medium;
      wherein the inlet port and the outlet port each include a valve constructed to remain closed until the cartridge is installed into a testing device used to test the gas detector.

18. A cartridge as set forth in claim 17 wherein the storage medium one of absorbs and adsorbs the detectable gas.

19. A cartridge as set forth in claim 17 wherein the storage medium has a porosity in an inclusive range of from about 80% to about 99%.

20. A test device for a gas detector configured to detect a detectable gas, the test device comprising:
   a receptacle defining a chamber for receiving therein a replaceable gas-releasing cartridge configured to release the detectable gas;
   an interface for fluidly coupling the test device to the gas detector such that gas is deliverable through the interface to the gas detector;
   passaging configured to provide fluid communication between the interface and both a gas-releasing cartridge received in the chamber and an external environment of the test device;
   a pump configured to pump air from the external environment and the detectable gas released from the gas-releasing cartridge received in the chamber through the passaging such that the pumped detectable gas and air form a proportioned mixture for testing the gas detector, the pump being configured to pump the proportioned mixture through the interface to the gas detector;
   an indicator, the indicator being configured to be selectively actuated to provide an indication of when the detectable gas is being released from the gas-releasing cartridge at a rate for forming the proportioned mixture; and
   an indicator controller configured to actuate the indicator based on a temperature signal representative of a temperature of the gas-releasing cartridge.

* * * * *